US012805781B2

(12) United States Patent
Sugiura

(10) Patent No.: US 12,805,781 B2
(45) Date of Patent: Nov. 24, 2026

(54) BIOSIGNAL SENSING ELECTRODE

(71) Applicant: Murata Manufacturing Co., Ltd., Nagaokakyo (JP)

(72) Inventor: Kosuke Sugiura, Nagaokakyo (JP)

(73) Assignee: MURATA MANUFACTURING CO., LTD., Nagaokakyo (JP)

(*) Notice: Subject to any disclaimer, the term of this patent is extended or adjusted under 35 U.S.C. 154(b) by 836 days.

(21) Appl. No.: 18/160,326

(22) Filed: Jan. 27, 2023

(65) Prior Publication Data

US 2023/0165500 A1 Jun. 1, 2023

Related U.S. Application Data

(63) Continuation of application No. PCT/JP2021/028615, filed on Aug. 2, 2021.

(30) Foreign Application Priority Data

Aug. 3, 2020 (JP) ................................ 2020-131864

(51) Int. Cl.
*A61B 5/25* (2021.01)
*A61B 5/263* (2021.01)

(52) U.S. Cl.
CPC ................ *A61B 5/25* (2021.01); *A61B 5/263* (2021.01)

(58) Field of Classification Search
CPC .................................. A61B 5/25; A61B 5/263
See application file for complete search history.

(56) References Cited

U.S. PATENT DOCUMENTS 6,253,099 B1 * 6/2001 Oskin ...................... A61B 5/28 600/372
9,579,055 B1 2/2017 Rood et al.
2008/0139953 A1 * 6/2008 Baker .................. A61B 5/0006 600/509
2008/0287770 A1 * 11/2008 Kurzweil ................. A61B 5/01 600/388

(Continued)

FOREIGN PATENT DOCUMENTS

WO 2019055784 A1 3/2019

OTHER PUBLICATIONS

Ling, Zheng, et al., "Flexible and conductive MXene films and nanocomposites with high capacitance", PNAS, Nov. 25, 2014 (Year: 2014).*

(Continued)

*Primary Examiner* — Adam Z Minchella
(74) *Attorney, Agent, or Firm* — ArentFox Schiff LLP

(57) ABSTRACT

A biosignal sensing that includes a conductive composite material containing particles of a layered material including one or plural layers and a polymer, the conductive composite material defining a contact surface with a subject, wherein the one or plural layers include a layer body comprising $Ti_3C_2$ and having a modifier or terminal T existing on a surface of the layer body, wherein the modifier or terminal T is at least one selected from the group consisting of a hydroxyl group, a fluorine atom, a chlorine atom, an oxygen atom, or a hydrogen atom, and the polymer is a hydrophilic polymer having a polar group, and the polar group is a group that forms a hydrogen bond with the modifier or terminal T of the layer.

12 Claims, 7 Drawing Sheets

(56) References Cited

U.S. PATENT DOCUMENTS

| | | | | |
|---|---|---|---|---|
| 2009/0021697 | A1* | 1/2009 | Burles | G03H 1/18 351/219 |
| 2014/0318699 | A1* | 10/2014 | Longinotti-Buitoni | A41D 1/002 156/247 |
| 2020/0405165 | A1 | 12/2020 | Vitale et al. | |

OTHER PUBLICATIONS

Driscoll et al., "Two-Dimensional Ti3C2 MXene for High-Resolution Neural Interfaces," ACS Nano, Sep. 2018, vol. 12, No. 10, pp. 10419-10429.

International Search Report in PCT/JP2021/028615, mailed Oct. 5, 2021, 6 pages.

Li et al., "Hydrophobic and Stable MXene—Polymer Pressure Sensors for Wearable Electronics," Applied Materials & Interfaces, Mar. 2020, vol. 12, No. 13, pp. 15362-15369.

Ling et al., "Flexible and conductive MXene films and nanocomposites with high capacitance," PNAS, Nov. 2014, vol. 111, No. 47, pp. 16676-16681.

Sharma et al., "Wearable Capacitive Pressure Sensor Based on MXene Composite Nanofibrous Scaffolds for Reliable Human Physiological Signal Acquisition," Applied Materials & Interfaces, Apr. 2020, vol. 12, No. 19, pp. 22212-22224.

* cited by examiner (a)

(b)

(a)

(b)

(c)

(a)

(b)

(c)

BIOSIGNAL SENSING ELECTRODE

CROSS REFERENCE TO RELATED APPLICATIONS

The present application is a continuation of International application No. PCT/JP2021/028615, filed Aug. 2, 2021, which claims priority to Japanese Patent Application No. 2020-131864, filed Aug. 3, 2020, the entire contents of each of which are incorporated herein by reference.

FIELD OF THE INVENTION

The present invention relates to a biosignal sensing electrode.

BACKGROUND OF THE INVENTION

Examples of a method for detecting biological information such as an electrical signal from a muscle or a heart of a subject (patient) without inflicting pain or the like on a human body include a method for measuring the biological information by bringing a sheet-like electrode into contact with the subject. In recent years, as the electrode, a dry electrode that does not require a gel or an adhesive and has an extremely low possibility of causing an allergic reaction to the skin of a patient has been proposed. For example, Patent Document 1 discloses a measuring device including a plurality of button-shaped electrodes embedded in or attached to a wearable worn around the torso of a pregnant subject as a device that enables non-invasive acquisition of an electrocardiogram signal and extraction of separate electrocardiogram signals of a fetus and a mother therefrom.

Patent Document 1: U.S. Pat. No. 9,579,055

SUMMARY OF THE INVENTION

The dry electrode of Patent Document 1 is provided with a protrusion in order to improve contact between the electrode and the skin, but this protrusion gives a strong discomfort to the patient. In addition, the dry electrode is required to have high conductivity and sufficiently high sensitivity in a dry state. The present invention has been made in view of the above circumstances, and an object of the present invention is to provide a biosignal sensing electrode capable of detecting biological information with high conductivity and high sensitivity without causing discomfort to a subject.

According to one gist of the present invention, there is provided a biosignal sensing electrode comprising: a conductive composite material containing particles of a layered material including one or plural layers and a polymer, the conductive composite material defining a contact surface with a subject, wherein the one or plural layers include a layer body comprising $Ti_3C_2$ and having a modifier or terminal T existing on a surface of the layer body, wherein the modifier or terminal T is at least one selected from the group consisting of a hydroxyl group, a fluorine atom, a chlorine atom, an oxygen atom, or a hydrogen atom, and the polymer is a hydrophilic polymer having a polar group, and the polar group is a group that forms a hydrogen bond with the modifier or terminal T of the layer.

According to the present invention, there is provided a biosignal sensing electrode comprising at least a conductive composite material containing particles of a predetermined layered material (also referred to as "MXene" in the present specification) and a polymer on a contact surface with a subject, in which the polymer is a hydrophilic polymer having a polar group, and the polar group is a group that forms a hydrogen bond with a modifier or terminal T of the layer, and thereby, biological information can be detected with high conductivity and high sensitivity without causing discomfort to a subject.

DETAILED DESCRIPTION OF THE INVENTION

Hereinafter, a biosignal sensing electrode and a conductive composite material used for the electrode in an embodiment of the present invention will be described in detail, but the present invention is not limited to such an embodiment.

(Conductive Composite Material)

Figure 1:
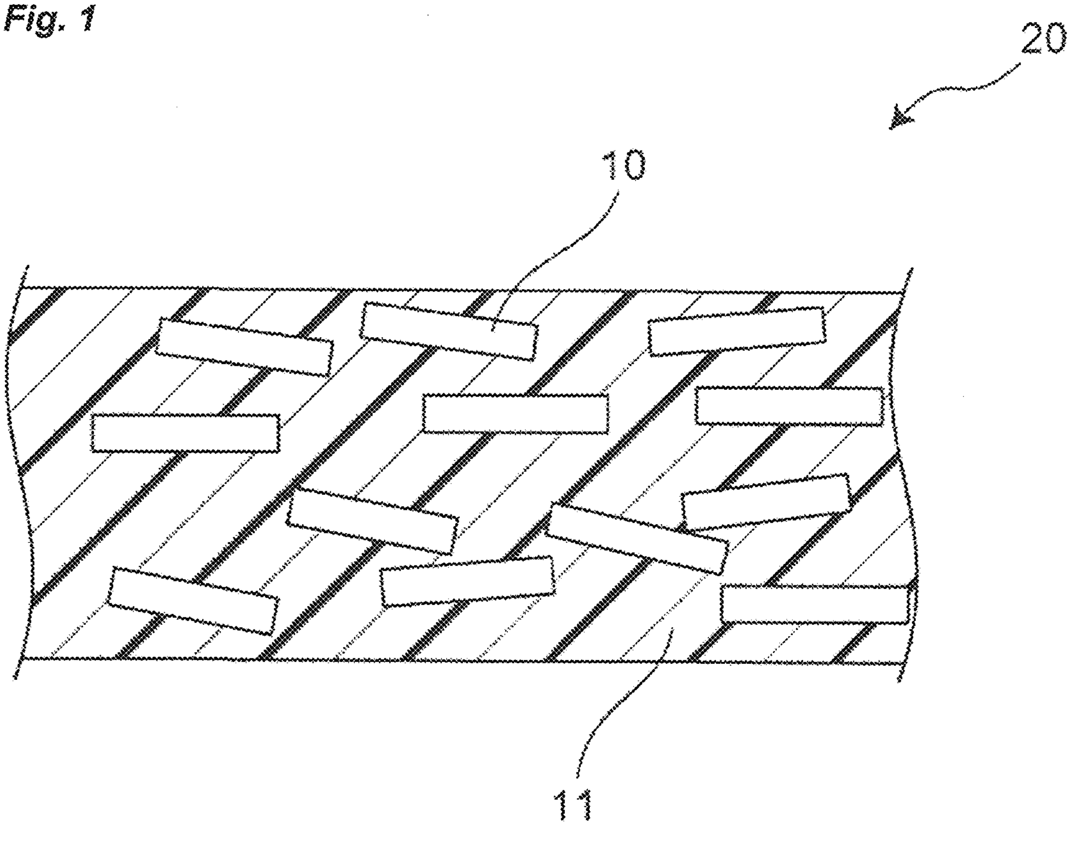
FIG. 1 is a schematic cross-sectional view illustrating a conductive composite material according to one embodiment of the present invention.

Referring to FIG. 1, a conductive composite material 20 used in the biosignal sensing electrode of the present embodiment comprises particles 10 of a predetermined layered material and a polymer 11. The polymer 11 is a hydrophilic polymer having a polar group, and the polar group is a group that forms a hydrogen bond with a modifier or terminal T of the particles 10 of the layered material.

Particles of a predetermined layered material in the present embodiment are defined as follows.

The particles 10 of the layered material containing one or plural layers, the one or plural layers containing a layer body represented by $Ti_3C_2$ (the layer body can have a crystal lattice in which each C is located in the octahedral array of Ti), and a modifier or terminal T existing on a surface of the layer body (more specifically, on at least one of two surfaces, facing each other, of the layer body), wherein T is at least one selected from the group consisting of a hydroxyl group, a fluorine atom, a chlorine atom, an oxygen atom, or a hydrogen atom (the layered material can be understood as a layered compound and also represented by "$Ti_3C_2T_x$" wherein x is any number and traditionally s or z may be used instead of x). Hereinafter, this layered material may be referred to as "$Ti_3C_2T_x$" or MXene (particles).

Such MXene can be synthesized by selectively etching (removing and optionally layer-separating) A atoms such as Al, Si, Sn, and In (and optionally parts of Ti atoms) from a MAX phase. The MAX phase is represented by $Ti_3AC_2$ and has a crystal structure in which a layer constituted by A atoms is located between two layers represented by $Ti_3C_2$ (each C may have a crystal lattice located in an octahedral array of Ti). When the number of Ti=the number of carbon atoms+1 as in $Ti_3AC_2$, the MAX phase has a repeating unit in which one layer of carbon atoms is disposed between the layers of Ti atoms of three layers (these layers are also collectively referred to as "$Ti_3C_2$ layer"), and a layer of A atoms ("A atom layer") is disposed as a next layer of the third layer of Ti atoms; however, the present invention is not limited thereto. By selectively etching (removing and optionally layer-separating) the A atoms (and optionally a part of the Ti atoms) from the MAX phase, the A atom layer (and optionally a part of the Ti atoms) is removed, and a hydroxyl group, a fluorine atom, a chlorine atom, an oxygen atom, a hydrogen atom, and the like existing in an etching liquid (usually, but not limited to, an aqueous solution of a fluorine-containing acid is used) are modified on the exposed surface of the $Ti_3C_2$ layer, thereby terminating the surface.

In the etching, an etching treatment is performed with an acid such as HF, HCl, HBr, HI, sulfuric acid, phosphoric acid, or nitric acid using a fluororesin container. For example, a method using a mixed liquid of lithium fluoride and hydrochloric acid, a method using hydrofluoric acid, or the like may be used. In the etching treatment, stirring is performed at a temperature of room temperature or higher and 40 degrees Celsius or lower for about 5 hours to 48 hours. Next, as a washing step, an operation of transferring a liquid after the etching treatment to, for example, a centrifuge tube, adding pure water thereto, stirring the mixture, separating a supernatant and a precipitate with a centrifugal separator, and discarding the supernatant may be repeated 5 times to 20 times. Thereafter, for example, the delamination treatment can be performed for a predetermined time using a mechanical shaker, a vortex mixer, a homogenizer, an ultrasonic bath, or the like. Subsequently, the supernatant and the precipitate are separated by a centrifugal separator, and the recovered supernatant can be used as a dispersion of $Ti_3AC_2$(MXene) in a monolayer form.

It is noted, in the present invention, MXene may contain remaining A atoms at a relatively small amount, for example, at 10 mass % or less with respect to the original amount of A atoms. The remaining amount of A atoms can be preferably 8 mass % or less, and more preferably 6 mass % or less. However, even if the remaining amount of A atoms exceeds 10 mass %, there may be no problem depending on the use and conditions of use of the paste (and the conductive film obtained thereby).

Figure 2:
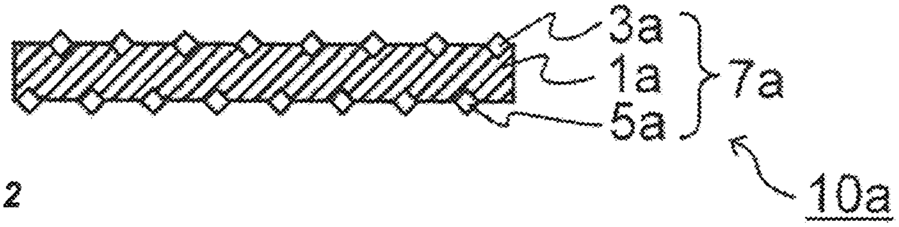
FIGS. 2(*a*) and 2(*b*) are schematic cross-sectional views illustrating MXene that is a layered material that can be used in a conductive composite material according to one embodiment of the present invention.
Figure 2:
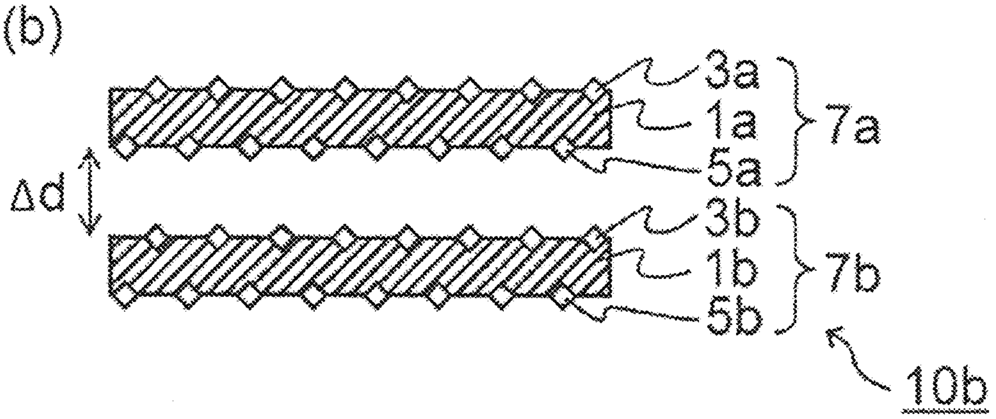

As schematically illustrated in FIGS. 2(*a*) and 2(*b*), the MXene (particles) 10 synthesized in this way can be a layered material containing one or plural MXene layers 7*a*, 7*b* (as examples of the MXene (particles) 10, FIG. 2(*a*) illustrates MXene 10*a* of one layer, and FIG. 2(*b*) illustrates MXene 10*b* of two layers, but is not limited to these examples). More specifically, the MXene layers 7*a*, 7*b* have layer bodies ($Ti_3C_2$ layers) 1*a*, 1*b* represented by $Ti_3C_2$, and modifiers or terminals T 3*a*, 5*a*, 3*b*, 5*b* existing on the surfaces of the layer bodies 1*a*, 1*b* (more specifically, on at least one of both surfaces, facing each other, of each layer). Therefore, the MXene layers 7*a*, 7*b* are also represented by "$Ti_3C_2T_x$," wherein x is any number. MXene 10 may be: one that exists as one layer obtained by such MXene layers being separated from one another (single layer structure illustrated in FIG. 2(*a*), so-called single-layer MXene 10*a*); a laminate made of a plurality of MXene layers being stacked to be apart from each other (multilayer structure illustrated in FIG. 2(*b*), so-called multilayer MXene 10*b*); or a mixture thereof. MXene 10 can be particles (which can also be referred to as powders or flakes) as a collective entity composed of the single-layer MXene 10*a* and/or the multilayer MXene 10*b*. In the present embodiment, MXene 10 is preferably particles (which can also be referred to as nanosheets), most of which are composed of the single-layer MXene 10*a*. In the case of the multilayer MXene, two adjacent MXene layers (for example, 7*a* and 7*b*) may not necessarily be completely separated from each other, but may be partially in contact with each other.

Although not limiting the present embodiment, the thickness of each layer of MXene (which corresponds to the MXene layers 7*a*, 7*b*) is, for example, 0.8 nm to 5 nm, and particularly 0.8 nm to 3 nm (which can vary mainly depending on the number of Ti atom layers included in each layer), and the maximum dimension in a plane (two-dimensional sheet plane) parallel to the layer is, for example, 0.1 μm to 200 μm, and particularly 1 μm to 40 μm. When the MXene is a laminate (multilayer MXene), for each laminate, an interlayer distance (alternatively, a void dimension, indicated by Δd in FIG. 2(*b*)) is, for example, 0.8 nm to 10 nm, particularly 0.8 nm to 5 nm, and more particularly about 1 nm. The total number of layers may be 2 or more, and is, for example, 50 to 100,000, particularly 1,000 to 20,000. The thickness in the lamination direction is, for example, 0.1 μm to 200 μm, particularly 1 μm to 40 μm. The maximum dimension in a plane (two-dimensional sheet plane) perpendicular to the lamination direction is, for example, 0.1 μm to 100 μm, and particularly 1 μm to 20 μm. Note that these dimensions can be obtained as a number average dimension (for example, a number average of at least 40) based on a photograph of a scanning electron microscope (SEM), a transmission electron microscope (TEM) photograph, or an atomic force microscope (AFM) photograph or a distance in a real space calculated from a position on a reciprocal lattice space of a (002) plane measured by an X-ray diffraction (XRD) method.

In the present embodiment, the polymer mixed with the particles of the layered material is a hydrophilic polymer having a polar group, and the polar group is a group that forms a hydrogen bond with a modifier or terminal T of the layer.

As the polymer, one or more polymers selected from the group consisting of water-soluble polyurethane, polyvinyl alcohol, sodium alginate, an acrylic acid-based water-soluble polymer, polyacrylamide, polyaniline sulfonic acid, or nylon are preferably used. Since these abundantly contain $—SO_3—$, —CONH—, —COO—, —OH, and —NH— in the molecular chain, they have high affinity with $Ti_3C_2T_x$, and for example, hydrogen bonds are likely to be formed, so that the resulting conductive composite material can be improved in conductivity by suppressing the randomness. As a result, a highly sensitive dry electrode can be provided.

Among these, one or more polymers selected from the group consisting of water-soluble polyurethane, polyvinyl alcohol, or sodium alginate are more preferable. It is considered that these polymers have a large number of functional groups that particularly contribute to hydrogen bond with $Ti_3C_2T_x$ among functional groups capable of forming hydrogen bonds, and thus, can easily form hydrogen bonds with $Ti_3C_2T_x$, and can provide a highly sensitive electrode. In particular, water-soluble polyurethanes are rich in urethane bonds having both hydrogen bond donor and hydrogen bond acceptor properties. The polyvinyl alcohol is rich in OH groups exhibiting a hydrogen bond donor property. In addition, the sodium alginate has high molecular flatness, and the number of functional groups capable of hydrogen bonding with MXene, particularly $Ti_3C_2T_x$, is substantially large.

As the polymer, a polymer having a urethane bond having both the hydrogen bond donor property and the hydrogen bond acceptor property is preferable, and from this viewpoint, the water-soluble polyurethane is particularly preferable. The polymer having a urethane bond mostly contributes to hydrogen bond with $Ti_3C_2T_x$. Specifically, when the modifier or terminal T in $Ti_3C_2T_x$ has at least one selected from the group consisting of a fluorine atom, a chlorine atom, or an oxygen atom as a hydrogen acceptor, H of NH of a urethane bond may act as a hydrogen donor to form a hydrogen bond. Further, when the modifier or terminal T in $Ti_3C_2T_x$ has a hydroxyl group and/or a hydrogen atom as a hydrogen donor, O of CO of the urethane bond may act as a hydrogen acceptor to form a hydrogen bond.

The ratio of the particles of the layered material, that is, the ratio of $Ti_3C_2T_x$ is preferably 52 mass % to 83 mass %. By setting the ratio of the particles of the layered material to 52 mass % or more, the biosignal can be detected with high sensitivity. The ratio of the particles of the layered material is more preferably 61 mass % or more. From the viewpoint of securing higher flexibility of the composite material, the ratio is preferably 83 mass % or less, and more preferably 75 mass % or less. The ratio of the particles of the layered material refers to a proportion in the conductive composite material. The conductive composite material of the present invention may contain additives such as a colorant and an antioxidant, but in this case, the ratio of the particles of the layered material refers to the proportion in the conductive composite material including the additives.

As another preferable embodiment, as the conductive composite material in which the particles of the layered material have a higher concentration, the ratio of the particles of the layered material is more than 83 mass % and 94 mass % or less. When the conductive composite material having an increased concentration is used, measurement can be performed without performing pretreatment such as removal of the corneum in advance even when it is difficult to detect a biosignal due to, for example, hardness of the corneum on the surface of the subject. From the viewpoint of detecting the biosignal with higher sensitivity, the ratio of the particles of the layered material is more preferably 85 mass % or more, still more preferably 89 mass % or more. Even in this case, from the viewpoint of securing the flexibility of the composite material, the ratio of the particles of the layered material is preferably 94 mass % or less, and more preferably 92 mass % or less.

As will be described later, two or more composite materials having different ratios of particles of the layered material may be provided in one electrode. In this case, at least a part of the conductive composite material satisfies the ratio of the particles of the layered material.

The conductive composite material in the biosignal sensing electrode of the present embodiment may be provided at least on the contact surface of the electrode with the subject, and is not limited to a specific form. Examples of the conductive composite material include a material in a solid state and a material in a soft state with flexibility. In a case where the conductive composite material has a sheet-like form, the thicknesses of the material can be measured by, for example, measurement with a micrometer, or by cross-sectional observation by a method using a scanning electron microscope (SEM), a microscope, a laser microscope, or the like.

The conductive composite material of the present embodiment preferably maintains a conductivity of 500 S/cm or more when the conductive composite material is in the form of a sheet having a film thickness of 5 μm, for example, as shown in Examples to be described later. The conductivity can maintain a conductivity of preferably 1,000 S/cm or more, more preferably 1,800 S/cm or more, still more preferably 2,400 S/cm or more, and even still more preferably 2,900 S/cm or more. The upper limit value of the conductivity of the conductive film is not particularly limited, and may be, for example, 20,000 S/cm or less. The conductivity can be determined as follows. That is, the surface resistivity is measured by a four-point probe method, a value obtained by multiplying the thickness [cm] by the surface resistivity [Ω/A] is the volume resistivity [Ω·cm], and the conductivity [S/cm] can be obtained as the reciprocal thereof.

(Biosignal Sensing Electrode)

The conductive composite material in the biosignal sensing electrode of the present embodiment may be provided at least on the contact surface with the subject, and is not limited to a specific form. Examples of the conductive composite materials are considered to include an electrode in a solid state and an electrode in a flexible and soft state, as described above.

Figure 3:
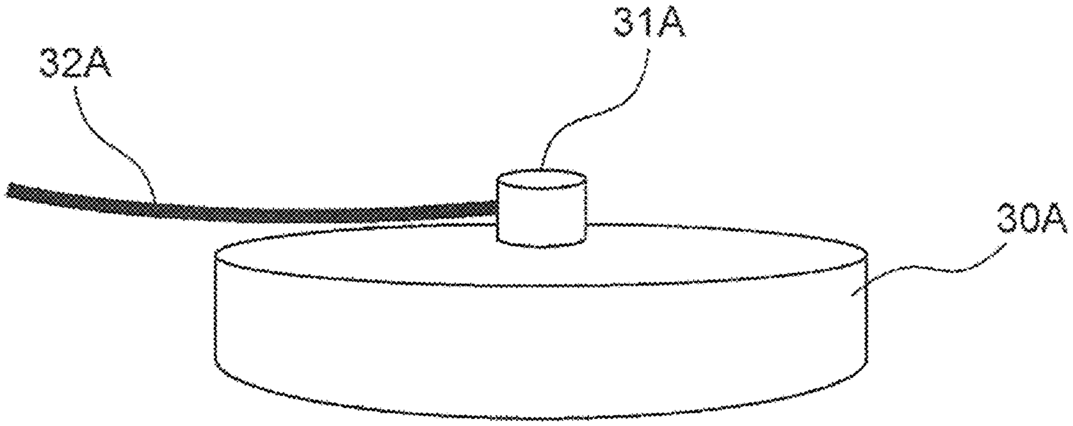
FIG. 3 is a schematic perspective view illustrating a biosignal sensing electrode according to one embodiment of the present invention.
Figure 4:
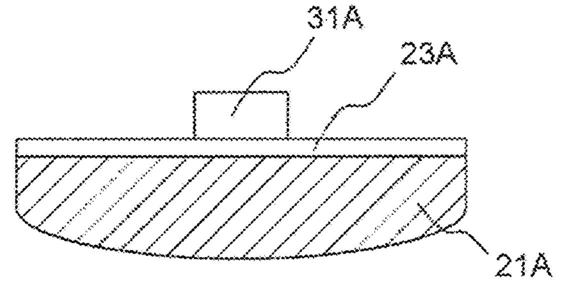
FIGS. 4(*a*) to 4(*c*) are schematic cross-sectional views illustrating a biosignal sensing electrode according to one embodiment of the present invention.
Figure 4:
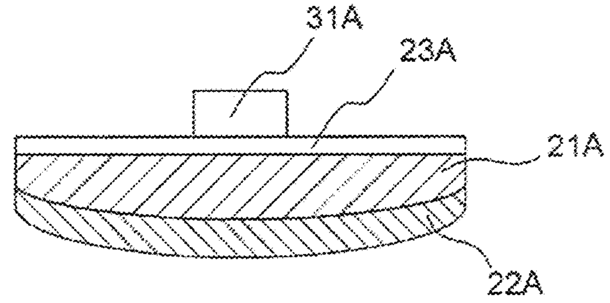
Figure 4:
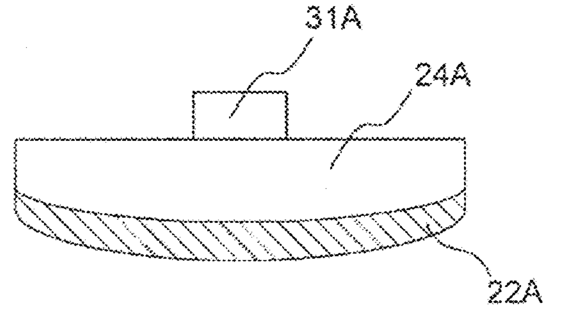
Figure 5:
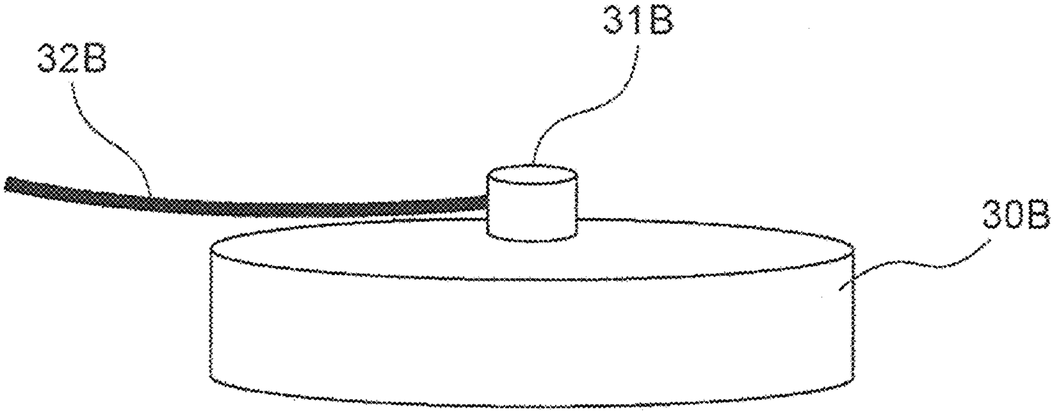
FIG. 5 is a schematic perspective view illustrating a biosignal sensing electrode according to another embodiment of the present invention.
Figure 6:
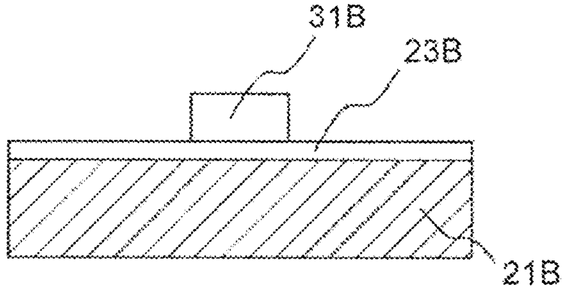
FIGS. 6(*a*) to 6(*c*) are schematic cross-sectional views illustrating a biosignal sensing electrode according to another embodiment of the present invention.
Figure 6:
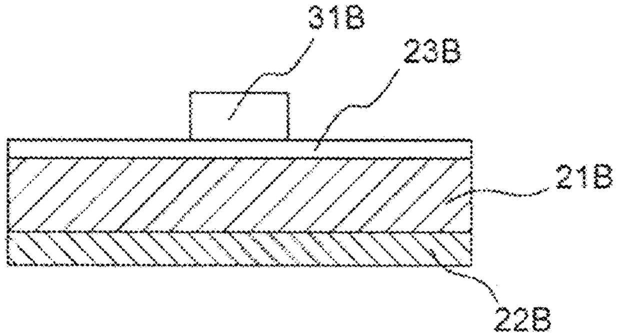
Figure 6:
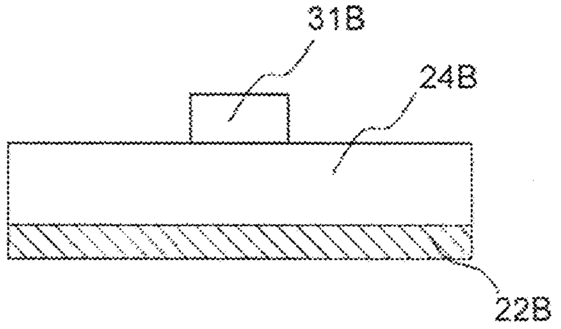

As an embodiment of the biosignal sensing electrode, FIG. 3 illustrates a schematic perspective view of a snap-type electrode. FIG. 3 is a diagram in which a lead wire 32A is connected to a snap portion 31A of an electrode 30A whose contact surface with the subject has a convex curved surface. FIG. 4(*a*), FIG. 4(*b*), and FIG. 4(*c*) illustrate cross-sectional views of the electrode 30A of FIG. 3. In addition, as another embodiment of the biosignal sensing electrode, FIG. 5 illustrates a schematic perspective view of a snap-type electrode in which a lead wire 32B is connected to a snap portion 31B of an electrode 30B whose contact surface with the subject is a flat surface. FIG. 6(*a*), FIG. 6(*b*), and FIG. 6(*c*) illustrate cross-sectional views of the electrode 30B of FIG. 5.

The embodiments of FIGS. 3 and 5 have the conductive composite material, and do not have protrusions like the electrode of Patent Document 1. The difference between the embodiments of FIGS. 3 and 5 is whether the contact surface with the subject is a curved surface or a flat surface. Therefore, except for this difference, FIGS. 4(*a*) and 6(*a*), FIGS. 4(*b*) and 6(*b*), and FIGS. 4(*c*) and 6(*c*) have the same structure.

In FIGS. 4(*a*) and 6(*a*), conductive composite materials 21A and 21B are respectively formed on substrates 23A and 23B formed of a conductive material. Since the conductive composite materials 21A and 21B are formed in this manner, a biosignal sensing electrode having high sensitivity can be provided. In particular, as illustrated in FIG. 4(*a*), since the contact surface with the subject is a curved surface, discomfort of wearing can be reduced.

Examples of the conductive material constituting the substrates 23A and 23B include at least one material of metal materials such as gold, silver, copper, platinum, nickel, titanium, tin, iron, zinc, magnesium, aluminum, tungsten, or molybdenum, and a conductive polymer. As the conductive composite materials 21A and 21B in FIGS. 4(*a*) and 6(*a*), for example, a conductive composite material in which a ratio of particles of the layered material is 52 mass % to 83 mass % can be used. As a result, it is possible to realize an electrode which is excellent in conductivity and flexibility and can further reduce discomfort of wearing.

In FIGS. 4(*b*) and 6(*b*), the conductive composite materials 21A and 21B are respectively formed on substrates 23A and 23B formed of a conductive material, and conductive composite materials 22A and 22B having a higher ratio of $Ti_3C_2T_x$ than the conductive composite materials 21A and 21B are respectively formed on contact surfaces with a subject. According to this configuration, since the conductive composite materials 22A and 22B having a high concentration of $Ti_3C_2T_x$ are formed on the contact surfaces with the subject, a biosignal sensing electrode having higher sensitivity can be provided. Therefore, for example, even in a case where it is difficult to detect the biosignal on the surface of the subject as in the case of a patient with a thick stratum corneum, the measurement can be performed without performing a pretreatment involving inflammation such as removing the stratum corneum in advance.

FIGS. 4(*b*) and 6(*b*) correspond to the biosignal sensing electrode in which the ratio of the particles of the layered material is higher in the contact portion with the subject than that in the non-contact portion with the subject. In particular, FIGS. 4(*b*) and 6(*b*) correspond to a biosignal sensing electrode in which the ratio of the particles of the layered material is higher on the side close to the contact portion with the subject, for example, higher in a region from the contact surface to about ⅓ of the thickness as compared with the ½ position of the thickness of the conductive composite material in the cross section of the electrode perpendicular to the contact surface with the subject. As illustrated in FIGS. 4(*b*) and 6(*b*), two or more conductive composite materials having different ratios of particles of the layered material may be stacked in one electrode. Alternatively, the conductive composite material may be provided such that the ratio of the particles of the layered material gradually or obliquely increases from the substrates 23A and 23B formed of the conductive material toward the contact surface with the subject.

As an aspect in which the ratio of the particles of the layered material in the contact portion with the subject is higher than that in the non-contact portion with the subject, there is an aspect in which the ratio of the particles of the layered material in the contact portion with the subject is more than 83 mass % and 94 mass % or less, and the ½ position of the thickness of the conductive composite material in the cross section of the electrode perpendicular to the contact surface with the subject is 52 mass % to 83 mass %.

FIGS. 4(*c*) and 6(*c*) illustrate electrodes in which conductive composite materials 22A and 22B having a high concentration of $Ti_3C_2T_x$ are respectively provided on contact surfaces of known snap-type electrodes 24A and 24B formed of a conductive material with a subject. As the conductive material constituting the snap-type electrodes 24A and 24B, the same material as the substrates 23A and 23B formed of the conductive material can be used. According to the above configuration, since the extraction electrode having versatility is used, it is possible to provide a biosignal sensing electrode with low cost and high sensitivity.

Although not illustrated, the conductive composite materials 21A and 21B in FIGS. 4(*a*) and 6(*a*) may be obtained by replacing $Ti_3C_2T_x$ with high-concentration conductive composite materials 22A and 22B.

Figure 7:
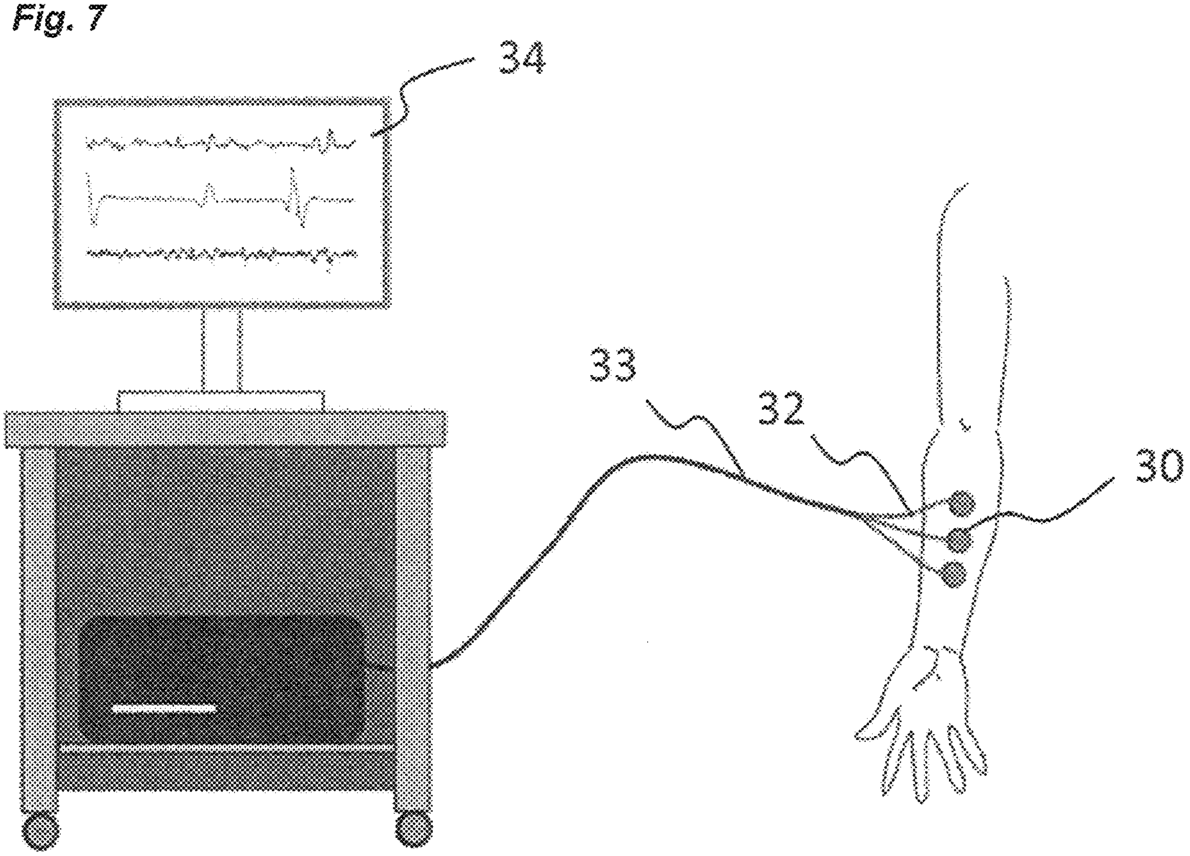
FIG. 7 is a schematic view illustrating a usage example of a biosignal sensing electrode according to one embodiment of the present invention.

As described above, when the conductive composite material containing $Ti_3C_2T_x$ is used, the impedance at the interface between the skin and the electrode is reduced as compared with the known electrode, and it is possible to detect a necessary signal without providing a protrusion. Therefore, as illustrated in FIG. 7, a plurality of the biosignal sensing electrodes 30 of the present embodiment may be attached to the skin of the arm of the subject to measure, for example, myoelectric potential. In FIG. 7, reference numeral 32 denotes a lead wire, reference numeral 33 denotes a cable, and reference numeral 34 denotes an analysis system.

A method for producing an electrode including the conductive composite material of the present embodiment using MXene produced as described above is not particularly limited. When the conductive composite material of the present embodiment has a sheet-like form, for example, as illustrated below, the layered material and the polymer can be mixed to form a coating film.

First, a MXene aqueous dispersion, a MXene organic solvent dispersion in which the MXene particles (particles of a layered material) are present in each solvent, or a MXene powder may be mixed with a polymer. The solvent of the MXene dispersion is typically water, and in some cases, other liquid substances may be contained in a relatively small amount (for example, 30 mass % or less, preferably 20 mass % or less based on the whole mass) in addition to water.

The stirring of the MXene particles and the polymer can be performed using a dispersing device such as a homogenizer, a propeller stirrer, a thin film swirling stirrer, a planetary mixer, a mechanical shaker, or a vortex mixer.

A slurry which is a mixture of the MXene particles and the polymer may be coated to a substrate (for example, a substrate), but the coating method is not limited. Examples of the coating method include a spray coating method in which spray coating is performed using a nozzle such as a one-fluid nozzle, a two-fluid nozzle, or an air brush, a slit coating method using a table coater, a comma coater, or a bar coater, a screen printing method, a metal mask printing method, a spin coating, and coating methods by immersion, or dropping. As described above, a substrate formed of a metal material, a resin, or the like suitable for the biosignal sensing electrode can be appropriately adopted as the substrate.

The coating and drying may be repeated a plurality of times as necessary until a film having a desired thickness is obtained. The drying and curing may be performed, for example, at a temperature of 400° C. or lower using a normal pressure oven or a vacuum oven.

Although the biosignal sensing electrode in one embodiment of the present invention has been described in detail above, various modifications are possible. It should be noted that the biosignal sensing electrode of the present invention may be produced by a method different from the producing method in the above-described embodiment.

EXAMPLES

Example 1

Preparation of MAX Particles

TiC powder, Ti powder, and Al powder (all manufactured by Kojundo Chemical Laboratory Co., Ltd.) were placed in a ball mill containing zirconia balls at a molar ratio of 2:1:1 and mixed for 24 hours. The obtained mixed powder was fired at 1350° C. for 2 hours under an Ar atmosphere. The fired body (block-shaped MAX) thus obtained was pulverized with an end mill to a maximum dimension of 40 μm or less. In this way, $Ti_3AlC_2$ particles were obtained as MAX particles.

Preparation of MXene Dispersion 1 g of the $Ti_3AlC_2$ particles (powder) prepared above was weighed, added to 10 mL of 9 mol/L hydrochloric acid together with 1 g of LiF using a fluororesin container, stirred with a stirrer at 35° C. for 24 hours for performing an etching treatment, and a solid-liquid mixture (suspension) containing a solid component derived from the $Ti_3AlC_2$ powder was obtained. The solid-liquid mixture (suspension) having been etched was transferred to a centrifuge tube, pure water was added thereto, the mixture was stirred, a supernatant and a precipitate were separated with a centrifuge, and the supernatant was discarded. This was repeated 10 times for washing. Thereafter, a delamination treatment was performed by performing a treatment for a predetermined time using a mechanical shaker. Thereafter, the supernatant was recovered by centrifugation, and the supernatant was used as a MXene dispersion.

The MXene dispersion, pure water, and each polymer shown in Table 1 were blended so as to obtain a MXene/polymer composite material in which the ratio of $Ti_3C_2T_x$ (after film formation and drying) was 52 mass % to 83 mass %, stirred with a propeller stirrer, and the obtained slurry was spray-coated on a PET film using a two-fluid nozzle. Irradiation with the spray and drying with a dryer were performed 15 times until the film thickness of the MXene/polymer composite material reached 5 After completion of the coating, the film was dried at 80° C. for about 30 minutes in an ambient pressure oven to obtain a MXene/polymer composite film.

Conductivity Measurement of MXene/Polymer Composite Material Film

The conductivity of the MXene/Polymer composite film was determined. For the conductivity, the surface resistivity (Ω) and the thickness (μm) were measured at three locations per sample. A value obtained by multiplying the thickness [cm] by the surface resistivity [Ω/A] was the volume resistivity [Ω·cm], and the conductivity [S/cm] was obtained as the reciprocal thereof. The arithmetic average value of the three conductivities thus obtained was adopted. The surface resistivity was measured by a four-point probe method. For the measurement of the surface resistivity, a low resistivity meter (Loresta AX MCP-T 370, manufactured by Mitsubishi Chemical Analytech) was used. In addition, a micrometer (MDH-25 MB, manufactured by Mitutoyo Corporation) was used for the thickness measurement. The results are shown in Table 1. The measurement accuracy of the conductivity is two significant digits (the same applies to Table 2 below.). In Table 1, a case where the conductivity was 500 S/cm or more was determined to be good (○), and a case where the conductivity was less than 500 S/cm was determined to be bad (×).

TABLE 1

| Types of MXene | Conductivity [S/cm] | Determination |
|---|---|---|
| $Ti_3C_2T_x$ | 4000 | ○ |
| $Ti_2CT_x$ | 100 | X |
| $Cr_2TiC_2T_x$ | 200 | X |
| $Cr_2VC_2T_x$ | 180 | X |

From the results in Table 1, as MXene to be mixed with the polymer, $Ti_3C_2T_x$ exhibits significantly higher conductivity than $Ti_2CT_x$, $Cr_2TiC_2T_x$, and $Cr_2VC_2T_x$, and by using $Ti_3C_2T_x$ having high conductivity, a highly sensitive electrode can be obtained.

Example 2

A MXene/polymer composite material film was prepared and the conductivity was measured in the same manner as in Example 1 except that $Ti_3C_2T_x$ was used as the type of MXene and each polymer shown in Table 2 was used as a polymer in addition to the water-soluble polyurethane. The results are shown in Table 2. In Table 2, a case where the conductivity was 2,900 S/cm or more was determined as very good (⊙), a case where the conductivity was less than 2,900 S/cm and 500 S/cm or more was determined as good (○), and a case where the conductivity was less than 500 S/cm was determined as bad (×).

TABLE 2

| Types of polymer | Conductivity [S/cm] | Determination |
|---|---|---|
| Organic polyurethane | 150 | X |
| Water-soluble polyurethane | 4000 | ⊙ |
| Polyvinyl alcohol | 3000 | ⊙ |
| Sodium alginate | 3500 | ⊙ |
| Acrylic acid-based water-soluble polymer | 1000 | ○ |
| Polyacrylamide | 950 | ○ |
| Polyaniline sulfonic acid | 900 | ○ |
| Nylon | 700 | ○ |
| Paraffin | 100 | X |

From the results in Table 2, when organic polyurethane and paraffin were used as the polymer, the conductivity of the composite material was low. The reason for this is considered as follows. First, paraffin (general term for alkane which is a kind of hydrocarbon compound and has 20 or more carbon elements) has low polarity, and therefore has low affinity with $Ti_3C_2T_x$, and the composite material to be prepared has high randomness, which is considered as the reason for the low conductivity. In addition, the organic polyurethane has low affinity between a slightly remaining organic solvent and $Ti_3C_2T_x$, and the composite material to be prepared has high randomness, which is considered as the reason for low conductivity.

On the other hand, a composite material of water-soluble polyurethane, polyvinyl alcohol, sodium alginate, an acrylic acid-based water-soluble polymer, polyacrylamide, polyaniline sulfonic acid, or nylon, and $Ti_3C_2T_x$ can realize a dry electrode having high conductivity and high sensitivity. As described above, it is considered that the polymers constituting the composite material in which the determination is ○ and ⊙ are rich in —$SO_3$—, —CONH—, —COO—, —OH, and —NH— in the molecular chain, and are likely to form a hydrogen bond with $Ti_3C_2T_x$. Among them, the composite material of water-soluble polyurethane, polyvinyl alcohol, or sodium alginate, and $Ti_3C_2T_x$, showed a sufficiently high conductivity of 3,000 S/cm or more. As a reason for this, it is considered that the polymer constituting the composite material for which these determinations were ⊙ has many functional groups contributing to hydrogen bond with $Ti_3C_2T_x$.

Most preferably, it is a composite material of $Ti_3C_2T_x$, and a water-soluble polyurethane. As described above, the water-soluble polyurethane has a large amount of functional groups contributing to hydrogen bond with $Ti_3C_2T_x$, and has good affinity with a subject containing a large amount of moisture unlike the organic polyurethane. In a case where the water-soluble polyurethane is present on the outermost surface of the composite material, it is considered that a biosignal is easily detected when the water-soluble polyurethane comes into contact with the subject.

The biosignal sensing electrode of the present invention can be preferably used as an electrode or the like for measuring, for example, EEG (electroencephalogram), ECG (electrocardiogram), EMG (electromyogram), or EIT (electrical impedance tomography) capable of detecting biological information such as an electrical signal from a muscle or a heart with high sensitivity without causing discomfort to a subject.

REFERENCE NUMERALS

1*a*, 1*b* layer body ($M_mX_n$ layer)
3*a*, 5*a*, 3*b*, 5*b* modifier or terminal T
7*a*, 7*b* MXene layer
10, 10*a*, 10*b* MXene (layered material)
11 polymer
20, 21A, 21B conductive composite material
22A, 22B high-concentration MXene conductive composite material
23A, 23B substrate formed of conductive material
24A, 24B conventional snap-type electrode
30, 30A, 30B biosignal sensing electrode
31A, 31B electrode snap portion
32, 32A, 32B lead wire
33 cable
34 analysis system

The invention claimed is:

1. A biosignal sensing electrode comprising:

a conductive composite material containing: particles of a layered material including one or plural layers; and a polymer, the conductive composite material defining a contact surface with a subject, wherein the one or plural layers include a layer body comprising $Ti_3C_2$ and having a modifier or terminal T existing on a surface of the layer body, wherein the modifier or terminal T is at least one selected from the group consisting of a hydroxyl group, a fluorine atom, a chlorine atom, an oxygen atom, or a hydrogen atom, the polymer is a hydrophilic polymer having a polar group, and the polar group is a group that forms a hydrogen bond with the modifier or terminal T of the one or plural layers, and the polymer is one or more selected from the group consisting of sodium alginate, an acrylic acid-based water-soluble polymer, polyacrylamide, polyaniline sulfonic acid, and nylon.

2. The biosignal sensing electrode according to claim 1, wherein a ratio of the particles of the layered material is 52 mass % to 83 mass %.

3. The biosignal sensing electrode according to claim 1, wherein a ratio of the particles of the layered material is more than 83 mass % and 94 mass % or less.

4. The biosignal sensing electrode according to claim 1, further comprising a conductive material substrate supporting the conductive composite material.

5. The biosignal sensing electrode according to claim 4, wherein a material of the conductive material substrate comprises at least one gold, silver, copper, platinum, nickel, titanium, tin, iron, zinc, magnesium, aluminum, tungsten, molybdenum, and a conductive polymer.

6. The biosignal sensing electrode according to claim 4, wherein the conductive composite material is a first conductive composite material, and the biosignal sensing electrode further comprises:

a second conductive composite material between the first conductive composite material and the conductive material substrate, wherein the first conductive composite material has a higher ratio of the particles of the layered material than the second conductive composite material.

7. The biosignal sensing electrode according to claim 6, wherein the ratio of the particles of the layered material in the first conductive composite material is more than 83 mass % and 94 mass % or less.

8. The biosignal sensing electrode according to claim 6, wherein a first ratio of the particles of the layered material in the first conductive composite material is more than 83 mass % and 94 mass % or less, and a second ratio of particles of layered material in the second conductive composite material is 52 mass % to 83 mass %.

9. The biosignal sensing electrode according to claim 1, wherein the contact surface defined by the conductive composite material is a convex curved surface.

10. The biosignal sensing electrode according to claim 1, wherein the contact surface defined by the conductive composite material is a flat surface.

11. A biosignal sensing electrode comprising:

a conductive composite material containing: particles of a layered material including one or plural layers; and a polymer, the conductive composite material defining a contact surface with a subject, wherein the one or plural layers include a layer body comprising $Ti_3C_2$ and having a modifier or terminal T existing on a surface of the layer body, wherein the modifier or terminal T is at least one selected from the group consisting of a hydroxyl group, a fluorine atom, a chlorine atom, an oxygen atom, or a hydrogen atom, the polymer is a hydrophilic polymer having a polar group, and the polar group is a group that forms a hydrogen bond with the modifier or terminal T of the one or plural layers, and a ratio of the particles of the layered material is higher on the contact surface with the subject as compared with a ½ position of a thickness of the conductive composite material in a cross section of the electrode perpendicular to the contact surface with the subject.

12. A biosignal sensing electrode comprising:

a conductive composite material containing: particles of a layered material including one or plural layers; and a polymer, the conductive composite material defining a contact surface with a subject, wherein the one or plural layers include a layer body comprising $Ti_3C_2$ and having a modifier or terminal T existing on a surface of the layer body, wherein the modifier or terminal T is at least one selected from the group consisting of a hydroxyl group, a fluorine atom, a chlorine atom, an oxygen atom, or a hydrogen atom, the polymer is a hydrophilic polymer having a polar group, and the polar group is a group that forms a hydrogen bond with the modifier or terminal T of the one or plural layers, and a first ratio of the particles of the layered material at the contact surface with the subject is more than 83 mass % and 94 mass % or less, and a second ratio of the particles of the layered material at a ½ position of a thickness of the conductive composite material in a cross section of the electrode perpendicular to the contact surface with the subject is 52 mass % to 83 mass %.

* * * * *